(12) United States Patent
Appling et al.

(10) Patent No.: US 10,696,005 B2
(45) Date of Patent: Jun. 30, 2020

(54) ASSEMBLY AND METHOD OF SAME FOR MECHANICALLY SKIVING TO REMOVE BALLOON PARISON TUBING MATERIALS

(71) Applicant: Freudenberg Medical, LLC, Carpinteria, CA (US)

(72) Inventors: Anthony Appling, Crestwood, KY (US); Scott Schewe, Eden Prairie, MN (US); Alan Yang, Edina, MN (US); Nao Lee, Brooklyn Park, MN (US)

(73) Assignee: FREUDENBERG MEDICAL, INC., Carpinteria, CA (US)

( * ) Notice: Subject to any disclaimer, the term of this patent is extended or adjusted under 35 U.S.C. 154(b) by 183 days.

(21) Appl. No.: 15/660,327

(22) Filed: Jul. 26, 2017

(65) Prior Publication Data

US 2018/0029325 A1 Feb. 1, 2018

Related U.S. Application Data

(60) Provisional application No. 62/368,600, filed on Jul. 29, 2016.

(51) Int. Cl.
*B32B 1/08* (2006.01)
*A61M 25/06* (2006.01)
(Continued)

(52) U.S. Cl.
CPC ........... *B32B 1/08* (2013.01); *A61M 25/0662* (2013.01); *A61M 25/1027* (2013.01); *B23B 3/06* (2013.01); *B23B 5/36* (2013.01); *B29C 48/0022* (2019.02); *B29C 48/03* (2019.02); *B29C 48/09* (2019.02); *A61M 25/1029* (2013.01); *B29C 48/022* (2019.02); *Y10T 82/25* (2015.01)

(58) Field of Classification Search
CPC .... B23B 5/36; B23B 3/02; B23B 3/06; B32B 1/08; A61M 25/1027; A61M 25/0662; A61M 25/1029; Y10T 82/25; B29C 48/09; B29C 48/0022; B29C 48/03; B29C 48/022
See application file for complete search history.

(56) References Cited

U.S. PATENT DOCUMENTS 3,735,461 A * 5/1973 Andrews, Sr. .......... B23B 29/12
407/86
4,054,068 A * 10/1977 Carter ................... B23B 29/043
82/158
(Continued)

*Primary Examiner* — Michael M. Robinson
(74) *Attorney, Agent, or Firm* — Dickinson Wright PLLC

(57) ABSTRACT

An assembly and method for mechanically skiving a tube to later form into a medical balloon are provided. The assembly includes a blade holder and a tube guide wherein the blade holder retains the blade in a diagonal relationship relative to the tube guide. A lathe assembly includes a mandrel for extending into a lumen of the tube and fitting into the tube guide. The lathe assembly further includes a spinning mechanism that rotates the mandrel relative to the blade for skiving the exterior surface of the polymer tube. The diagonal relationship allows for precise shaping of a transition portion of the tube, which is located between a medially located un-skived portion of tube and two skived portions located at tube ends. Once the tube is skived, a molding process inflates the un-skived portion into a balloon and stretches the transition portion and the skived portions forming a medical balloon.

12 Claims, 6 Drawing Sheets

(51) Int. Cl.
*B29C 48/03* (2019.01)
*B23B 3/06* (2006.01)
*B23B 5/36* (2006.01)
*B29C 48/00* (2019.01)
*A61M 25/10* (2013.01)
*B29C 48/09* (2019.01)

(56) References Cited

U.S. PATENT DOCUMENTS

| | | | | |
|---|---|---|---|---|
| 4,058,033 | A | * | 11/1977 | Lahm .................. B23B 3/06 82/121 |
| 4,636,117 | A | * | 1/1987 | Shikata .............. B23B 27/1622 407/104 |
| 5,541,092 | A | | 7/1996 | Kirk et al. |
| 5,733,301 | A | | 3/1998 | Forman |
| 5,826,588 | A | | 10/1998 | Forman |
| 6,193,738 | B1 | * | 2/2001 | Tomaschko ........... A61M 25/10 606/194 |
| 6,488,654 | B2 | | 12/2002 | Gonzalez et al. |
| 6,719,774 | B1 | | 4/2004 | Wang |
| 7,217,278 | B2 | | 5/2007 | Tomaschko et al. |
| 7,771,450 | B2 | | 8/2010 | Tomaschko et al. |
| 8,357,177 | B2 | | 1/2013 | Tomaschko et al. |
| 8,764,705 | B2 | | 7/2014 | Hennessey |
| 8,986,339 | B2 | | 3/2015 | Warnack |
| 2002/0072707 | A1 | * | 6/2002 | Gonzalez ......... A61M 25/1027 604/103.06 |
| 2006/0182873 | A1 | | 8/2006 | Klisch et al. |
| 2016/0022967 | A1 | | 1/2016 | Burton |
| 2016/0045275 | A1 | | 2/2016 | Schneider et al. |

\* cited by examiner

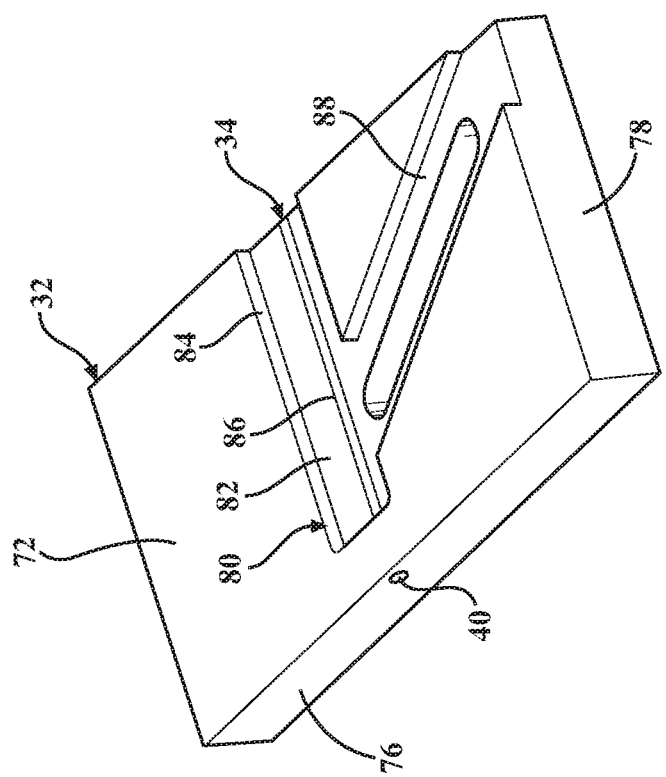
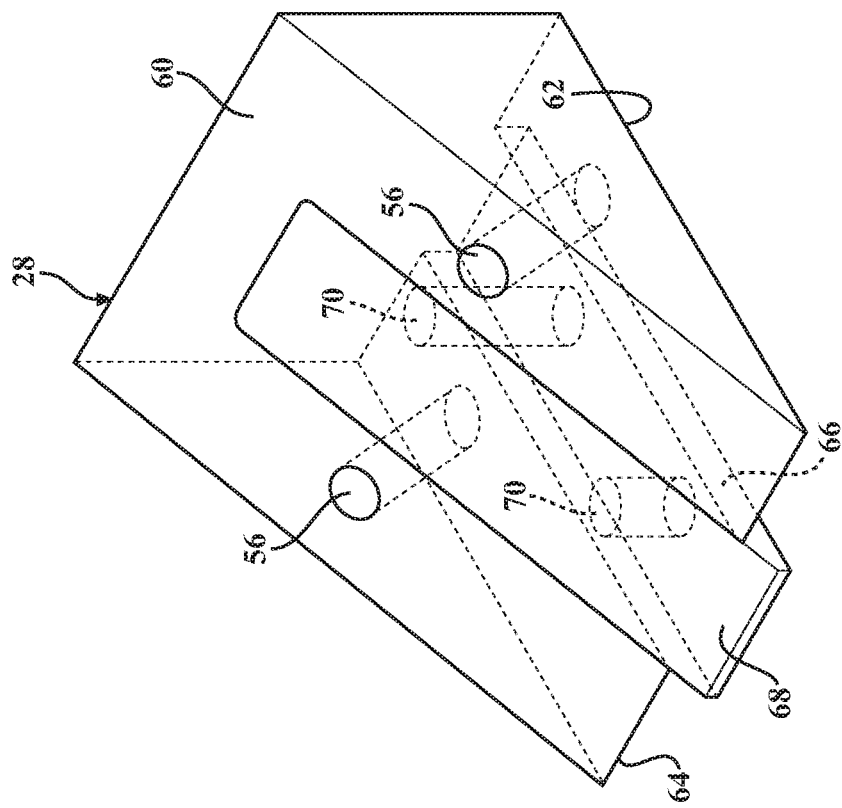

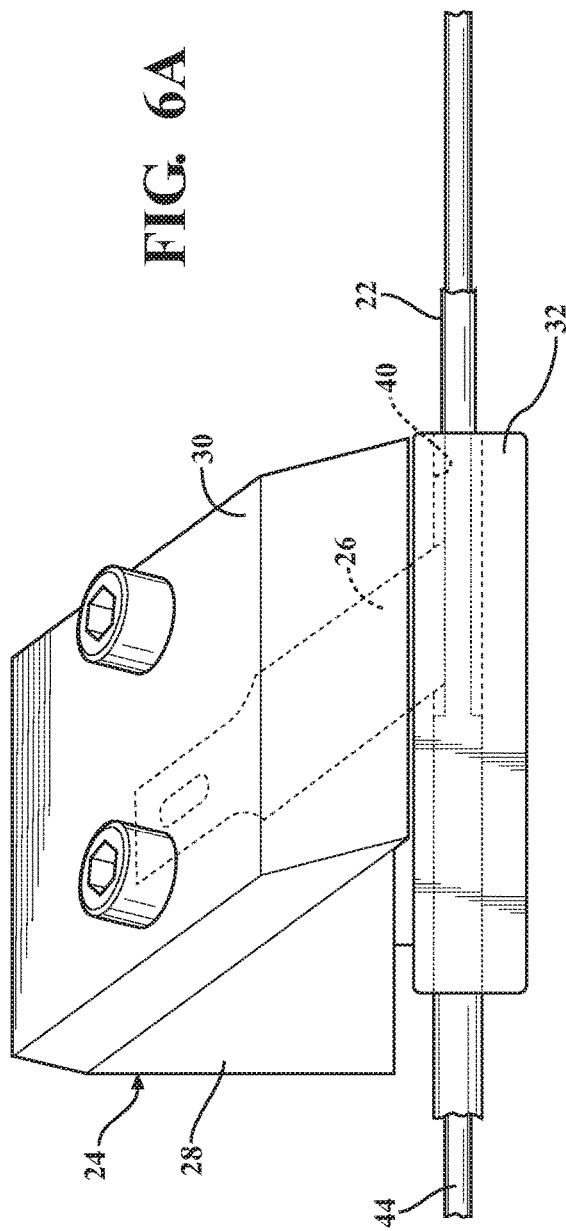
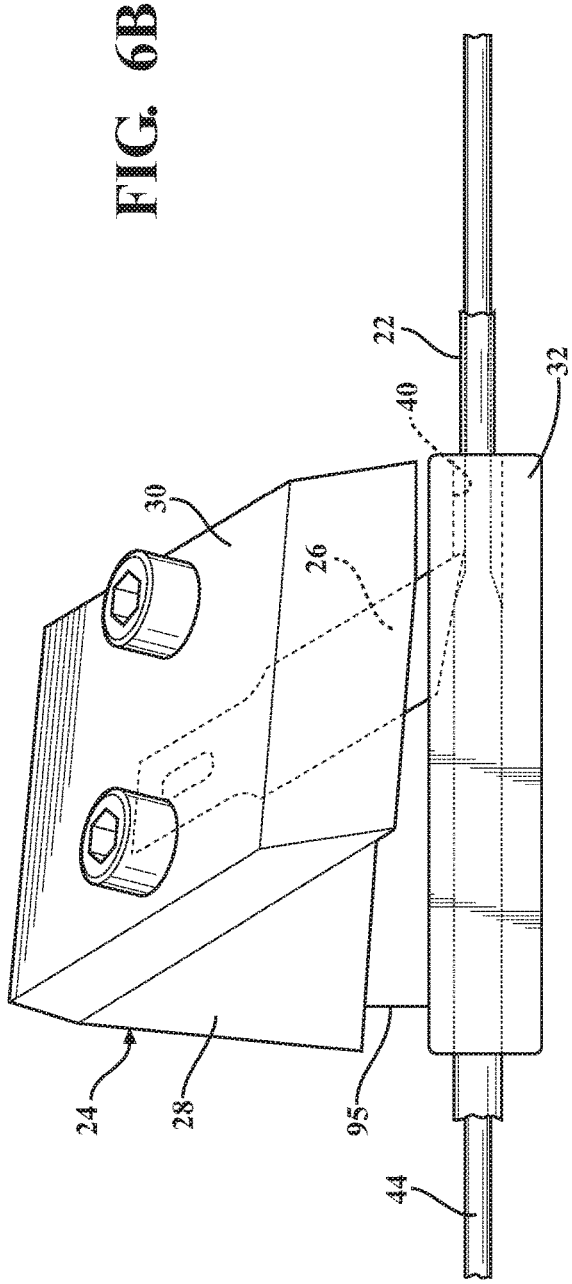

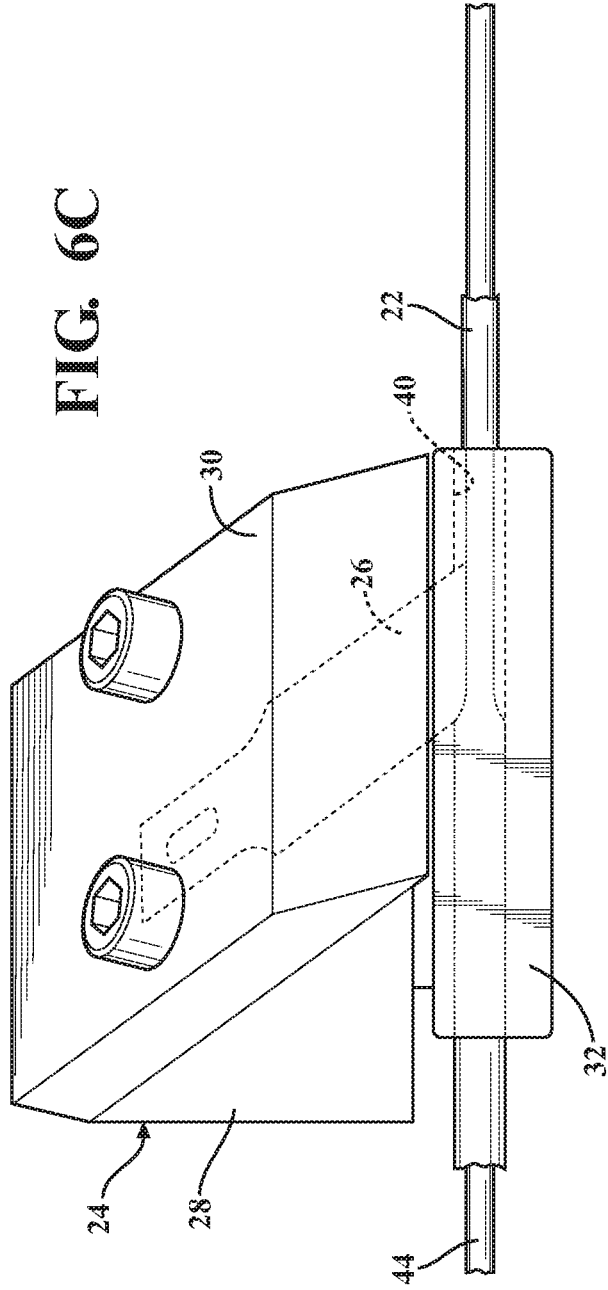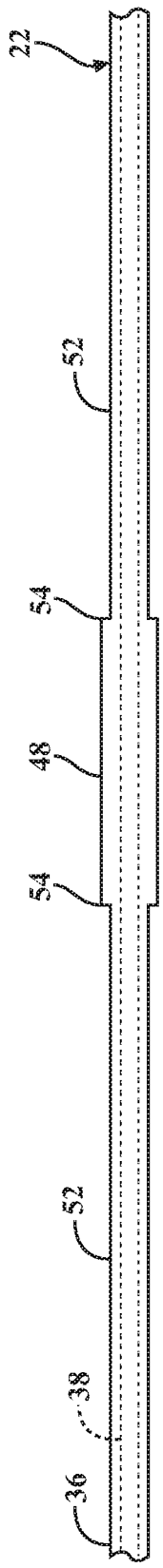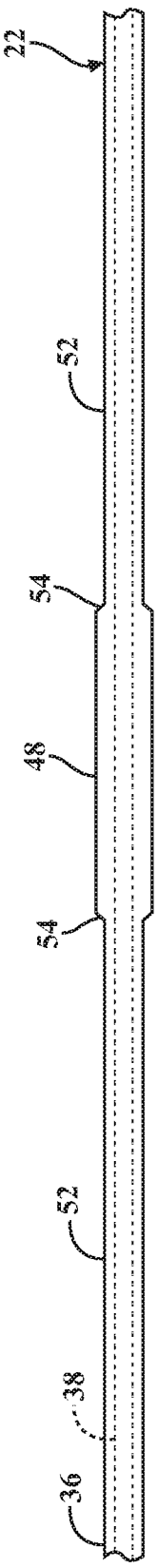

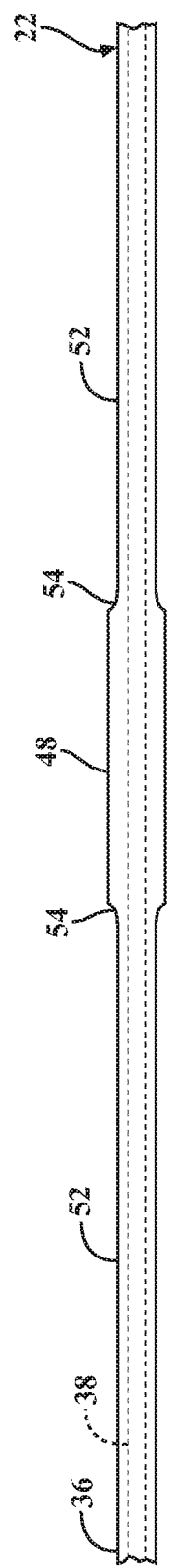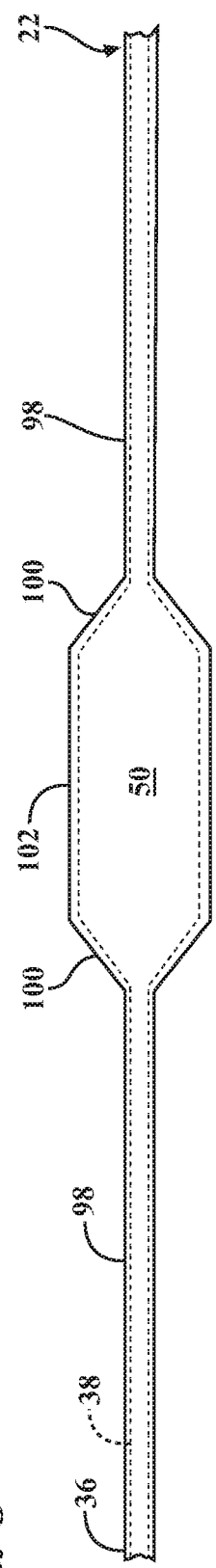

ASSEMBLY AND METHOD OF SAME FOR MECHANICALLY SKIVING TO REMOVE BALLOON PARISON TUBING MATERIALS

CROSS REFERENCE TO RELATED APPLICATION

This U.S. Utility Patent Application claims the benefit of and priority to U.S. Provisional Patent Application Ser. No. 62/368,600, filed Jul. 29, 2016, the entire disclosure of the application being considered part of the disclosure of this application, and hereby incorporated by reference.

BACKGROUND OF THE INVENTION

1. Field of the Invention

The present disclosure is generally related to selective removal of tubing material. More specifically, the present disclosure is related to an assembly and method of mechanically skiving to selectively remove tubing materials to later form into a medical balloon.

2. Related Art

This section provides background information related to the present disclosure which is not necessarily prior art.

Dilatation balloons are utilized in a variety of medical procedures where dilating the target area can provide a therapeutic effect. For example, in coronary angioplasty a catheter with an inflatable balloon at its distal end is guided through the vascular system until the balloon is positioned within the stenosis. The balloon is then inflated with a liquid media through a lumen within the catheter that inflates and distends the balloon to dilate the stenosis and provide improved blood flow for the patient. Several of the most important performance features of the balloon catheter is track-ability (ability to safely navigate the tortuous vasculature), crossing profile (ability to traverse across a tight stenosis with the least of amount of force), re-cross profile (ability to cross a second stenosis after an initial balloon inflation) and a safe burst failure mode (consistent longitudinal failure plane).

Typical balloons tend to have a significant increase in wall thickness as the balloon wall thickness transitions from the body portion (thinnest wall) through the cone portion (increasing wall thickness) into the waist portion (thickest wall). This is a result of the ever decreasing "blow out ratio" or the ratio of tube diameter to final balloon diameter. This condition leads to a variety of design and performance issues ranging from larger initial lesion crossing profiles due to excess wall material, increased resistance to balloon rewrap to the smallest diameter profile possible upon deflation in preparation to treat another lesion. The most serious effect is adverse bursting failure modes where the material in the cone portion is proportionally thicker than in the body portion, increasing the risk of a dangerous radial failure mode during burst, which in extreme events can cause a piece of balloon material to tear off and embolize in the blood stream.

Coronary, peripheral and many other medical balloons are typically blow molded from a solid hollow polymer tube. Typically, a balloon made from an unaltered tube or parison will have proportionately thicker wall thicknesses in the cones and waist as a functional of the hoop ratio in that portion of the balloon. To alleviate this issue, the tube is typically modified to include a larger cross sectional area of polymeric material in the body portion and less of this material in the cone or the waist area that tapers to facilitate joining to a catheter shaft. There are many ways to modify this tube to prepare it for the subsequent molding or blow out stage. These methods include modifying the tube by localizing heat on the portion of the balloon tubing, which enables a localized reduction of cross sectional area by stretching. Conversely, another method can utilize extreme cold temperature to drive the polymer further into a glassy state and protect the portion of the tube intended to make up the body portion of the balloon by preventing a designated portion of the tubing from stretching. One side effect of this type of process is the increased level of molecular orientation of the polymer chains. When the tube is blow molded into a balloon these localized areas of increased molecular orientation in the areas that make up the balloon cones and waist portions tend to have a thinner wall thickness but at the expense of decreased flexibility in those portions of the balloon. A balloon made with a process as described above will tend to have an increased crossing profile as it will be more difficult to fold to an ideal diameter due to the increased stiffness and the increased longitudinal molecular orientation of those segments. It will also tend to decrease flexibility of the formed tubing in those localized areas making the balloon more difficult to track through tortuous vessel anatomy.

Other methods of modifying a balloon wall thickness for enhanced performance include "cone grinding", such as disclosed in U.S. Pat. No. 6,193,738, where the balloon is modified by using a centerless grinder to selectively remove material in discrete areas of the balloon that will ultimately make up the cone and the waist portions of the finished balloon. While this technique works to enable a reduced wall thickness in the cone and waist portion of a balloon, it can also lead to an increase in adverse failure modes and it is limited to concentric material removal or at best a slightly tapered material removal profile.

Thus, a need exists to continue development of new and improved methods of forming dilatation balloons that advance the art and provide enhanced functionality.

SUMMARY OF THE INVENTION

The subject invention provides an assembly for mechanically removing material from a tube defining a lumen via skiving, wherein the skived polymer tube can later be converted into a medical balloon. The assembly includes a blade holder and a tube guide wherein the blade holder retains a blade in a diagonal relationship relative to the tube guide. A lathe assembly includes a mandrel for extending into the lumen and fitting into the tube guide. A lathe assembly further includes a spinning mechanism that rotates the mandrel relative to the blade for skiving the exterior surface of the polymer tube.

It should be appreciated that the invention also provides a method for converting a tube into a medical balloon. The method begins with providing a tube having an exterior surface and an interior surface bounding a lumen and a blade. Next, the tube and the blade are brought together in a diagonal relationship wherein the tube and blade are rotated relative to one another with a spinning mechanism. As the tube and blade are rotated relative to one another, skiving of the tube is initiated as the blade and tube come into rotational contact.

BRIEF DESCRIPTION OF THE DRAWINGS

The drawings described herein are for illustrative purposes only of selected embodiments and are not intended to limit the scope of the present disclosure. The inventive concepts associated with the present disclosure will be more readily understood by reference to the following description in combination with the accompanying drawings wherein:

FIG. 4 perspective view of a bottom wedge portion of the unassembled blade holder assembly;

FIG. 5 is a perspective view of the support holder illustrating a tube guide and a recess that aligns the blade holder in a diagonal relationship to the tube guide in accordance with another example embodiment;

FIGS. 6A-6C are side views of the blade holder and the support holder skiving the tube according to example embodiments;

FIG. 7A-7C are a side views of the skived tubes from the example embodiments of the blade holder configurations provided in 6A-6C; and FIG. 8 is a side view a molded balloon stretched from an un-skived portion of the tube;

DESCRIPTION OF THE ENABLING EMBODIMENTS

Example embodiments will now be described more fully with reference to the accompanying drawings. In general, the subject embodiments are directed to an assembly and method of mechanically skiving to selectively remove balloon tubing material. However, the example embodiments are only provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Figure 1:
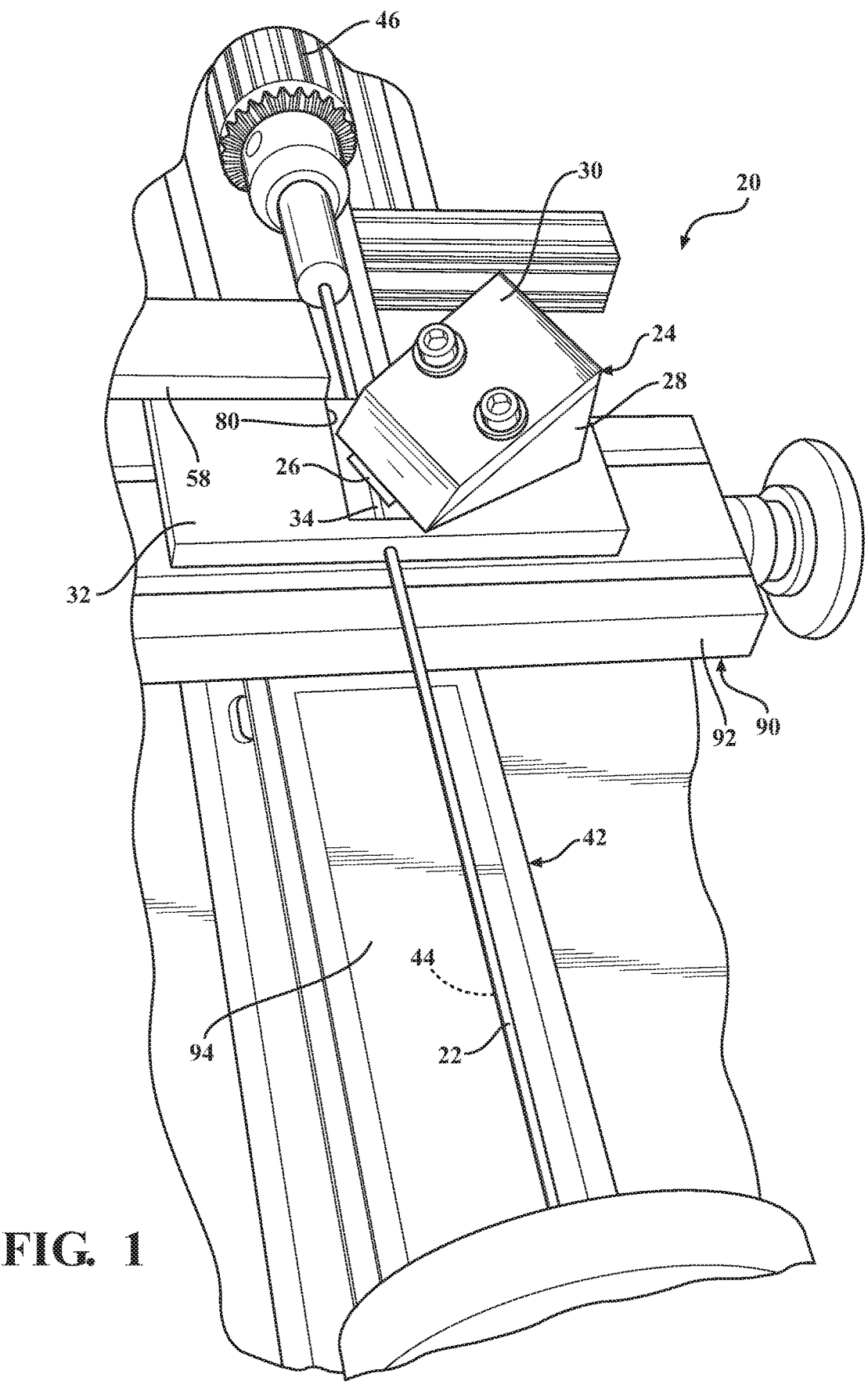
FIG. 1 is a perspective view of assembly for use in the subject method including a lathe assembly and a blade holder skiving a tube, according to an example embodiment.
Figure 3:
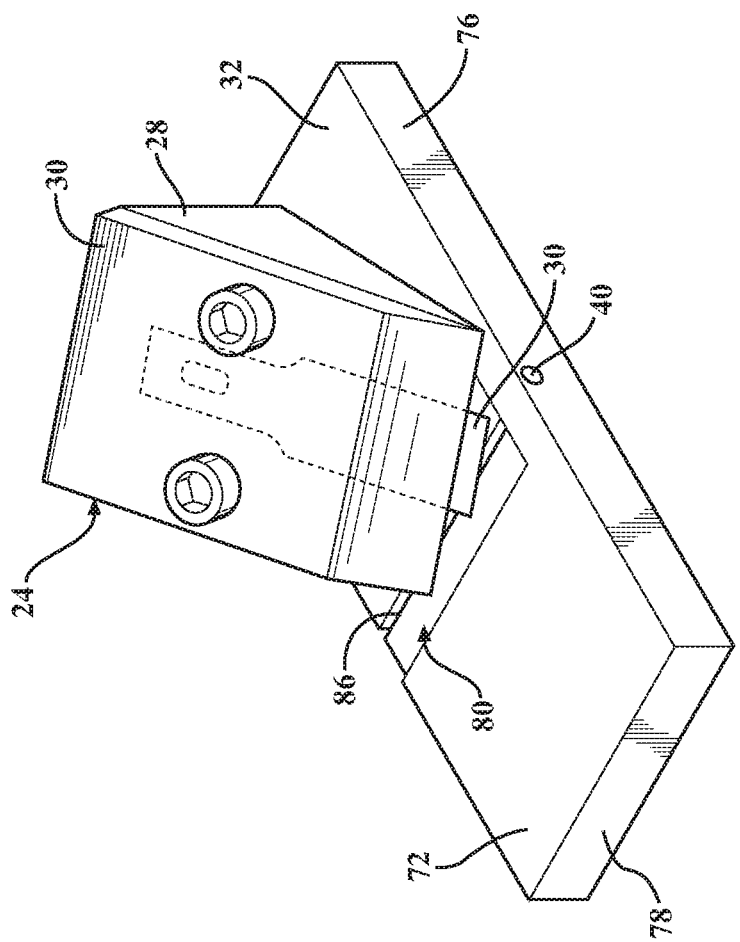
FIG. 3 is a perspective view of the blade holder assembly secured to the support holder.
Figure 2:
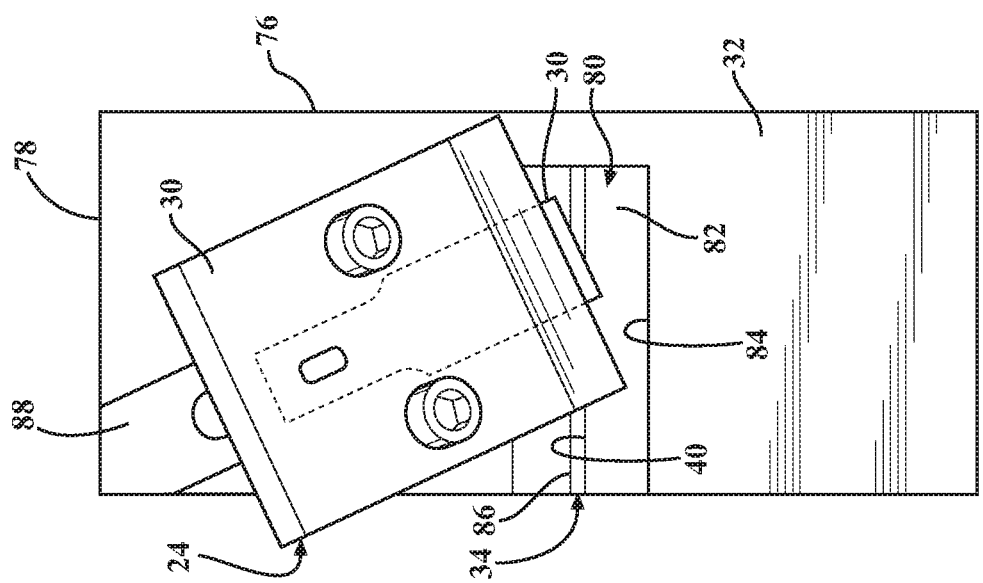
FIG. 2 is a top view of the blade holder assembly secured to a support holder.

Referring to the Figures, wherein like numerals indicate corresponding parts throughout the several views, the invention provides an assembly 20, generally shown in FIG. 1, for removing material from a tube 22 via a skiving process. As best illustrated in FIGS. 1 and 2, the assembly 20 utilizes a blade holder 24 which secures a blade 26 between a bottom wedge portion 28 and a top plate portion 30. A support holder 32 defines a tube guide 34 for placement of the tube 22 during skiving. The tube 22 includes an outer wall 36 defining an outer diameter and an inner wall 38 bounding a lumen defining an inner diameter. The tube guide 34 is defined by a cylindrical wall 40 having an equal or greater diameter to the outer diameter of the raw extruded tube 22 to add rigidity to the tube 22 during the shaping/skiving process. The blade holder 24 can engage the support holder 32 in a connected relationship wherein the blade 26 rests at a diagonal angle across the tube guide 34.

A lathe assembly 42 includes a mandrel 44 having an outer diameter equal or less than the inner diameter of the tube 22 for placing in the lumen. The lathe assembly 42 further includes a chuck 46 selectively holding the mandrel 44 and the tube 22 from at least one end and spinning it relative to the blade 26. By spinning the mandrel 44 and the tube 22 relative to the blade 26, the blade 26 removes material from the outer wall 36 of the tube 22, by sliding the support holder 32 transversely along the mandrel 44 and tube 22, the blade 26 decreases the outer diameter of the tubing the length that the support holder 32 is moved. The skiving will generally be applied from opposite ends of the tube 22, until the un-skived portion 48, which will later be formed into a balloon 50, is medially spaced between skived portions 52. In this manner, a transition portion 54 is formed between the skived portions 52 and the medially spaced un-skived portion 48.

As best illustrated in FIG. 4, the bottom wedge portion 28 and the top plate portion 30 of the blade holder 24 each define corresponding apertures 56 for placing fasteners therein that when fastened, clamp the blade 26 therebetween. The blade 26 can be changed by loosening the fasteners and spacing the bottom wedge portion 28 and the top plate portion 30. The bottom wedge portion 28 includes an angled top surface 60 and a flat bottom surface 62 that merge at a reinforcement edge 64. The flat bottom surface 62 defines a rib 66 extending transversely past the reinforcement edge 64 to define a blade reinforcement 68. Fastener holes 70 extend into the rib 66 for connection to the support holder 32.

As illustrated in FIG. 6A, the blade 26 can sit at a diagonal angle, i.e., a transverse angle relative to the tube guide 34 when the top wedge portion and the support holder 32 are in the connected relationship. When the blade 26 sits at a diagonal angle, the transition portion 54 will essentially be a right angle step as shown in FIG. 7A. The blade 26 can also sit at a compound angle i.e., an angle both transverse and axial relative to the tube guide 34, as illustrated in FIGS. 6B and 7B wherein the spinning blade 26 skives the tube 22 forming a conically shaped transition portion 54 between the skived portions 52 and un-skived portion 48. Furthermore, the blade 26 could include a non-rectilinear edge. For example, the blade 26 could have an arced portion and a flat portion, wherein the arced portion skives the tubing first and the flat portion creates the uniform cylindrical shape of the tubing until the blade 26 stops before the un-skived portion 48. In this manner the skiving with a non-rectilinear edge will creating an arc-shaped fillet transition portion 54 between the skived portions 52 and the un-skived portion 48 as best shown in FIGS. 6C and 7C. In a preferred embodiment, the blade 26 sits at an angle relative to the tube 22 between 20° and 70° and even more preferably closer to 45°. However, it should be appreciated that the blade could sit at any angle relative to the tube 22 and could have utilize several different edges without departing from the subject invention.

As shown in FIG. 5, the support holder 32 includes a top support surface 72 and a bottom support surface extending between a pair of first edges 76 spaced by pair of second edges 78. The top support surface 72 includes a groove 80 disposed between and in a parallel relationship with the second edges 78 and extending from one of the first edges 76 and terminating in a spaced relationship to the other of the first edges 76. The groove 80 is defined by a groove floor 82 and groove walls 84. The groove floor 82 defines a blade slot 86 that exposes the cylindrical wall 40 along the groove 80. The cylindrical wall 40 extends from one of the first edges 76 along the groove floor 82 through one of the groove walls 84 to another of the first edges 76. The top support surface 72 further defines a recess 88 having a stepped profile extending through the bottom support surface and disposed in an angled relationship to the groove 80. The profile of the recess 88 matches the rib 66 of the bottom wedge portion 28 and both engage in the connected relationship. The bottom wedge portion 28 can be fixed to the support holder 32 with fasteners extending tough the recess 88 of the support holder 32 into the fastener holes 70 of the rib 66.

Referring back to FIG. 1, the lathe assembly 42 further includes a sliding mechanism 90 and a carriage 92 for connecting to the support holder 32. The connection between the carriage 92 and the support holder 32 is accomplished with a clamp 58. However, it should be appreciated that there are many ways of connecting the support holder 32 to the carriage 92 without departing from the subject invention. The carriage 92 rests on a track 94 and is mechanically driven along the track 94 at a constant speed. The carriage 92 could be driven by a lead screw (not expressly shown) or any other device that can push the carriage 92 along the track 94 at a substantially constant speed. The track 94 is parallel to the mandrel 44 and thus moves the carriage 92 and support holder 32 axially along the spinning tube 22 and mandrel 44 in contact with the blade 26.

The invention further includes a method of mass removal via skiving that can be utilized to remove material from an extruded tube 22. As best illustrated in FIGS. 1 and 6A-C, the method includes providing a blade holder 24 which is used to secure a blade 26 for use during skiving of the tube 22 as well as a support holder 32 which includes and defines a tube guide 34. The tube guide 34 has an inner diameter equal to or greater than the outer diameter of the raw extruded tube 22 to add rigidity to the tubing 22 during the shaping/skiving process. As best illustrated in FIG. 2, the blade holder 24 assembly 20 is placed on top of the support holder 32 so that the blade 26 sits at a diagonal across the tube guide 34. Shims 95 may be needed between the blade holder 24 and the support holder 32, and if used the shim 95 will typically travel the length of the blade holder 24 assembly 20. The shims 95 can be utilized to define the depth of skiving by spacing the blade holder 24 from the support holder 32. The shims 95 may also assist in spacing the blade holder 24 from the support holder 32 at a compound angle, by being wedge-shaped. Thus different cutting depths and angles can be accomplished without changing out the blade 26.

As best illustrated in FIG. 1, the method provides a lathe assembly 42 which includes a mandrel 44 for entering the lumen from an end of the tube 22. The mandrel 44 and tube 22 are then slide into the tube guide 34. The mandrel 44 and the tube 22 are then connected to a chuck 46 that is then rotated preferably at a speed between 150 rpm and 3000 rpm. Although, generally if rotation speeds above 150 rpm are used, at step of external cooling will be needed to maintain the polymer tube 22 below the glass transition temperature. While the tube 22 is often referred to as being polymer, it should be appreciated that the tube could comprise different material without departing from the scope of the invention and thus there may be different cooling requirements for other compositions.

As best illustrated in FIG. 1, the blade holder 24 is placed on a carriage 92 and then introduced to a rotating tube 22 to skive away a portion of the outer diameter of the tube 22 and reduce the cross section area up to 50% or more of the original cross sectional area of the tube 22 wall. The blade holder 24 assembly 20 is slowly pushed or moved forward along the tube 22 on the carriage 92 at a constant speed until the predetermined length of skiving along the tube 22 is reached. The step of moving the carriage 92 is generally done mechanically by providing a lead screw mechanism or the like. During this movement and skiving action, it is important that there is a constant pressure pushing back—too fast and you will have huge divot spirals, too slow and the chip will break off and the cut will essentially fail.

The blade 26 can be shaped to create a depth of cut transition between the original outer diameter, i.e., the un-skived portion 48 and the reduced outer diameter areas, i.e., the skived portion 52. For example, many different transition patterns could be utilized and created, such as a straight line to line transition, a step transition, a filleted transition, or the like as illustrated best in FIGS. 7A-C. Each of these transitions will yield slightly different thickness profiles in the finished balloon 50. If temperature of the tube 22 rises during the skiving process beyond the glass transition temperature of the polymer, external cooling would be employed to ensure the polymer substrate stays below the glass transition temperature (Nylons=40-50° C. glass transition). This could be accomplished by including a method step of cooling the metal reinforcement mandrel 44, the skiving blade 26 or providing an external cooling liquid or gas ($CO_2$, nitrogen, Argon, chlorofluorocarbon, or the like) to the polymer tube 22 during the skiving process.

The method of mechanically skiving to selectively remove tubing material to later form a balloon 50 will now be more specifically described with relation to an exemplary 14 mm diameter, 80 mm length PTA balloon 50. However, the 14 mm diameter and 80 mm length dimensions of the balloon 50 are simply utilized as an example, and different diameters and lengths of balloon 50 could be utilized without departing from the scope of the subject disclosure.

The method begins by obtaining an extruded tube 22. For example, the extruded tube 22 could be a Vestamid ML24 nylon 12" tube 22, having a size of 0.138" outer diameter, 0.094" inner diameter, and a wall thickness of 0.027". However, other sizes of the extruded tube 22 could be utilized without departing from the scope of the subject disclosure. The extruded tube 22 is then cut to approximately 200 mm (plus or minus 2 millimeters) in length and then loaded over a 0.09" OD stainless steel mandrel 44 which is then loaded into the lathe assembly 42. When the steel mandrel 44 is loaded into the lathe assembly 42, the end of the tube 22 abuts the skiving blade 26 and is secured in a chuck 46 for rotation. In this position, the mandrel 44 is free to rotate about an axis.

The method proceeds by initiating rotation of the mandrel 44 at a speed between 150 rpm-3000 rpm. As best illustrated in FIG. 5, once the part is up to rotation speed, movement of the skiving fixture/blade 26 is initiated utilizing a traverse speed suitable for the tube size. For example, in an exemplary embodiment, the skiving blade 26 traverses down the tube 22 at approximately 5 mm/sec and removes 90 mm of length to an outer diameter ~0.125" (~30% wall removed) on the distal end of the tube 22. The part is unloaded and remounted in the opposite orientation to facilitate an identical material removal depth of approximately 78 mm of length on the proximal end. Once complete, and with reference to FIG. 6, the method results in a partially skived tube 22, i.e., a parison, which includes a main un-skived portion 48 spaced medially between two skived portions 52. In a preferred, but non-limiting, embodiment, the main un-skived portion 48 is approximately 32 mm in length.

The method proceeds by stretching the partially skived tube 22 at room temperature, until all of the skived portions 52 have been fully elongated, leaving the 32 mm of the un-skived portion 48 in an un-stretched state. The skived portions 52 of the tube 22 are then trimmed to facilitate introduction into an 0.056" inner diameter heated necking die (115° C.-150° C.), then pulled through the heated die up to the un-stretched and un-skived portion 48. Once up to the un-skived portion 48, the tube 22 is quickly removed from the necking die to prevent heat from transferring to the un-skived portion 48 and increasing crystallinity in that zone. The necking process is then repeated on the other end of the tube 22. The necking process results in a shaped tube 22 or parison, such as that illustrated in FIG. 8 that is ready for molding.

Molding consists of loading the shaped tube 22 into a molding machine (not expressly shown) and securing both ends of the shaped tube 22 with pneumatic grippers. The shaped tube 22 is heated to soften the plastic and simultaneous introduce high pressure gas. The combination of heat, pressure and longitudinal stretching will convert the shaped tube 22 into the balloon 50. A completed, fully molded balloon 50 with skived portions 48 stretched into waist portions 98 (placed outside of where the waist portions 98 will be trimmed) is exemplary shown in FIG. 8. The tensioning step where longitudinal movement is enabled can be modified to elongate (or pull) the length of the transition portion 54 to define a cone portion 100 to facilitate attachment to a catheter. This step of elongating the transition portion 54 to a cone portion 100 could elongate the transition portion 54 by 50% or more. Put another way, the method can be adjusted to alter the amount of shaped tube 22, i.e., parison, utilized in the finished balloon 50 component. With reference to FIG. 8, generally speaking the greatest overall benefit will come from leaving as much of the transition portion 54 in the cone portion 100 of a body portion 102 that includes the balloon 50 to minimize wall thickness in that zone. However, in certain embodiments, the transition portion of an unmolded tube 22 will only comprise part, 50% as an exemplary example, of the cone portion 54 once molded. In other words, part of the un-skived portion 48 and part of the skived portion 52 could also be molded into part of the cone portion 100 which does not have to be molded exclusively from the transition portion 54 of the tube 22. The transition between the skived portions 52 to un-skived portions 48 can be placed outside of where the waist portions 98 of the balloon 50 would be cut to later be fitted onto a catheter.

It should be appreciated that the foregoing description of the embodiments has been provided for purposes of illustration. In other words, the subject disclosure it is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varies in many ways. Such variations are not to be regarded as a departure from the disclosure, and all such modifications are intended to be included within the scope of disclosure.

What is claimed is:

1. An assembly for mechanically removing material from a tube defining a lumen comprising:
    a lathe assembly including a mandrel for extending into the lumen prior to skiving;
    a support holder defining a tube guide for placement of said mandrel and the tube;
    said support holder having a top support surface defining a groove disposed in parallel relationship with said tube guide and extending downwardly from said top support surface to a groove floor;
    said groove floor defining a slot being open to at least a portion of said tube guide;
    said top support surface defining an angled recess disposed in angled relationship with said groove;
    a blade holder disposed within said angled recess and holding a blade in a diagonal relationship relative to said slot for cutting the tube placed within the tube guide during a skiving process;
    said blade holder including a bottom wedge portion and a top plate portion having a clamped position for holding said blade and an unclamped position for releasing and changing said blade;
    said bottom wedge portion including an angled top surface and a flat bottom surface that merge at a reinforcement edge and a rib extending downwardly from said flat bottom surface and transversely past said reinforcement edge to define a blade reinforcement; and
    said lathe assembly including a spinning mechanism for rotating said mandrel relative to said blade.

2. An assembly as set forth in claim 1 wherein said lathe assembly includes a sliding mechanism for sliding said blade axially relative to the mandrel at a constant speed.

3. An assembly as set forth in claim 2 wherein the sliding mechanism includes a carriage and a track for moving said blade holder and said blade jointly and axially along said mandrel.

4. An assembly as set forth in claim 1 wherein said blade holder holds the blade at a compound angle relative to said mandrel.

5. An assembly as set forth in claim 1 wherein the blade includes an edge that is non-rectilinear.

6. An assembly as set forth in claim 1 including shims spacing said support holder and said blade holder for selecting a depth and angle defining the relationship between said blade and said tube guide.

7. An assembly as set forth in claim 1 wherein said blade holder retains said blade in a diagonal relationship with said slot at an angle between 20° and 70°.

8. An assembly as set forth in claim 1 wherein said groove floor extends along a plane disposed in transverse relationship to said tube guide to define said slot.

9. An assembly as set forth in claim 1 wherein said rib of said bottom wedge portion is disposed within said angled recess of said top support surface to establish a connected relationship between said blade holder and said support guide.

10. An assembly as set forth in claim 9 wherein said top support surface defines an elongated aperture extending downwardly from said recess and said bottom wedge portion defines a plurality of fastener holes for receiving fasteners extending through said elongated aperture and into said plurality of fastener holes to secure said bottom wedge portion to said blade holder.

11. An assembly as set forth in claim 9 wherein a profile of said rib matches a profile of said recess.

12. An assembly as set forth in claim 1 wherein said support guide extends between a pair of first edges spaced by a pair of second edges and said groove extends from one of said first edges and terminates in spaced relationship to the other of said first edges.

* * * * *